(12) United States Patent
Toth

(10) Patent No.: US 10,363,533 B2
(45) Date of Patent: Jul. 30, 2019

(54) DOUBLE ZONE TUBULAR REACTOR AND METHOD FOR CARRYING OUT MALEIC ANHYDRIDE PRODUCTION BY N-BUTANE OXIDATION

(71) Applicant: Technobell d.o.o. Koper, Koper (SI)

(72) Inventor: Gabor Toth, Szekesfehervar (HU)

(73) Assignee: Technobell d.o.o. Koper, Koper (SI)

( * ) Notice: Subject to any disclaimer, the term of this patent is extended or adjusted under 35 U.S.C. 154(b) by 0 days.

(21) Appl. No.: 15/891,941

(22) Filed: Feb. 8, 2018

(65) Prior Publication Data

US 2018/0229201 A1 Aug. 16, 2018

(30) Foreign Application Priority Data

Feb. 10, 2017 (EP) ..................................... 17155726

(51) Int. Cl.
*B01J 8/06* (2006.01)
*C07D 307/60* (2006.01)

(52) U.S. Cl.
CPC ............ *B01J 8/067* (2013.01); *C07D 307/60* (2013.01); *B01J 2208/00017* (2013.01); *B01J 2208/0053* (2013.01); *B01J 2208/00132* (2013.01); *B01J 2208/00221* (2013.01); *B01J 2208/00256* (2013.01); *B01J 2208/021* (2013.01)

(58) Field of Classification Search
CPC .............................. B01J 8/067; C07D 307/60
USPC ......................................................... 422/659
See application file for complete search history.

(56) References Cited

U.S. PATENT DOCUMENTS

| 3,147,084 | A | * | 9/1964 | Franzen | .................... | B01J 8/067 |
| | | | | | | 165/140 |
| 3,448,054 | A | * | 6/1969 | Gordon | .................... | C09K 5/12 |
| | | | | | | 252/71 |
| 3,871,445 | A | * | 3/1975 | Wanka | .................... | B01J 8/067 |
| | | | | | | 165/104.14 |
| 4,562,269 | A | * | 12/1985 | Moorehead | ............... | C07C 5/48 |
| | | | | | | 502/209 |

(Continued)

OTHER PUBLICATIONS

European Patent Office, Extended European Search Report, Application No. 17155726.7, 10 pages, dated Jun. 27, 2017.

(Continued)

*Primary Examiner* — Huy Tram Nguyen
(74) *Attorney, Agent, or Firm* — Sunstein Kann Murphy & Timbers LLP

(57) ABSTRACT

A tubular reactor that produces maleic anhydride from a gas mixture containing n-butane and oxygen includes a first reaction zone including an inlet for the gas mixture and a second reaction zone including an outlet for a reaction gas mixture, a plurality of tubes extending in an axial direction through the first and second reaction zones, a temperature control system, configured for controlling a reaction temperature in each of the reaction zones independently, includes a heat transfer system for each of the reaction zones configured for controlling the temperature of a liquid coolant flowing through one of the reaction zones, and a circulation pumping system configured for controlling flow conditions of the liquid coolant flowing through the reactor and one of the heat transfer systems, and a preheating arrangement configured for preheating the gas mixture such that the gas mixture enters the first reaction zone at a predefined inlet temperature.

35 Claims, 6 Drawing Sheets

(56) References Cited

U.S. PATENT DOCUMENTS

| | | | |
|---|---|---|---|
| 5,161,605 A * | 11/1992 | Gutlhuber | B01J 8/067 |
| | | | 165/103 |
| 6,191,332 B1 | 2/2001 | Duee et al. | |
| 6,803,473 B2 | 10/2004 | Weiguny et al. | |
| 2004/0236120 A1* | 11/2004 | Hibst | C07D 307/60 |
| | | | 549/259 |
| 2007/0088092 A1 | 4/2007 | Klanner et al. | |
| 2008/0269521 A1* | 10/2008 | Hammon | B01J 8/067 |
| | | | 562/532 |
| 2009/0043114 A1* | 2/2009 | Taheri | B01J 8/067 |
| | | | 549/257 |
| 2010/0036157 A1 | 2/2010 | Ko et al. | |
| 2011/0008218 A1 | 1/2011 | Woo et al. | |

OTHER PUBLICATIONS

Wellauer, et al., "Optimal policies in maleic anhydride production through detailed reactor modelling," Chemical Engineering Science, vol. 41, Issue 4, 1986, 2 pages (abstract).

* cited by examiner

DOUBLE ZONE TUBULAR REACTOR AND METHOD FOR CARRYING OUT MALEIC ANHYDRIDE PRODUCTION BY N-BUTANE OXIDATION

CROSS-REFERENCE TO RELATED APPLICATIONS

The present application claims the benefit of EP 17 155 726.7 filed Feb. 10, 2017, the disclosure of which is incorporated by reference herein in its entirety.

FIELD OF THE INVENTION

The present invention is in the field of maleic anhydride production. In particular, the present invention relates to a tubular reactor for carrying out maleic anhydride production by means of n-butane oxidation as well as to a corresponding method.

BACKGROUND OF THE INVENTION

Maleic anhydride ($C_2H_2(CO)_2O$) is an important intermediate product in several large-scale industrial applications related for example to polymers and coatings. Industrial preparation of maleic anhydride is usually carried out inside tubular reactors in which the partial oxidation of n-butane with air takes place in presence of a catalyst in order to accelerate the reaction and hence to increase the reaction yield, i.e. the amount of maleic anhydride obtained. The catalyst usually comprises vanadium pentoxide and phosphorus pentoxide, which are rather expensive. Therefore, a main goal in the industrial production of maleic anhydride is to achieve a high reaction yield over a long period of time while simultaneously ensuring a long life-cycle of the catalyst.

Maleic anhydride is typically produced by means of vapor-phase partial oxidation of n-butane ($C_4H_{10}$) with air according to the reaction:

$$C_4H_{10} + 3.5O_2 \rightarrow C_4H_2O_3 + 4H_2O \quad (1)$$

However, several parallel reactions inevitably take place, in particular the following reactions:

$$C_4H_{10} + 4.5O_2 \rightarrow 4CO + 5H_2O$$

$$C_4H_{10} + 6.5O_2 \rightarrow 4CO_2 + 5H_2O$$

$$C_4H_{10} + 2.5O_2 \rightarrow 2CH_3COOH + H_2O$$

$$C_4H_{10} + 2.5O_2 \rightarrow 4/3 CH_2CHCOOH + 7/3 H_2O$$

The net production of maleic anhydride depends on the conversion rate of n-butane on the one hand, that is, the amount of n-butane oxidising, and the reaction selectivity on the other hand, that is, the relative amount of n-butane reacting according to reaction (1) leading to the production of maleic anhydride. Both the conversion rate and the reaction selectivity strongly depend on temperature and on the throughput of n-butane.

All of the above reactions are highly exothermic, although to different extents. The conversion of n-butane into maleic anhydride according to reaction (1) releases for example about 350 kcal/mole, whereas the conversion of n-butane into carbon dioxide releases about 650 kcal/mole. When the above reactions take place inside a reactor, the resulting reaction heat therefore needs to be dissipated. For this purpose, a heat transfer agent, typically a liquid coolant, is made to flow through the reactor at a temperature and flow rate appropriate for absorbing the reaction heat generated inside the reactor.

A typical tubular reactor 100 for producing maleic anhydride known in the prior art is shown in FIG. 1. The tubular reactor 100 has a cylindrical shape and a circular cross-section with a hole in the middle, such that the reactor 100 has a toroidal geometry. A plurality of tubes, typically between 5000 and 30,000 tubes are arranged between the inner wall and the outer wall of the toroid and are configured for being filled with a catalyst. In FIG. 1, only three tubes 124 of said plurality exemplary shown on illustrative purposes. The tubes 124 cross the reactor 100 in vertical direction and communicate with one or more inlets 1, through which the reacting gas mixture can enter the reactor, at one of their ends and with one or more outlets 18, through which the reacted gas mixture can exit the reactor, at the other one of their ends. A circulation pumping arrangement 22 drives a flow of a liquid coolant through the reactor 100 among the tubes 124. After circulating through the reactor 100, the liquid coolant is circulated through a heat exchanger 21 that cools down the liquid coolant before the liquid coolant re-enters the reactor to undergo a further cooling cycle.

In the tubular reactor 100 of FIG. 1, the liquid coolant generally flows in the same direction as the reacting gas mixture, which in the figure corresponds to the upward vertical direction. The flow is however additionally directed in the radial direction of the reactor alternatingly inwards and outwards by a plurality of baffles 6, 7, 8, 9, 12, 13, and 14 in order to distribute the flow of liquid coolant such that the flow of liquid coolant reaches each of the plurality of tubes 124 in which the reaction takes place.

In general, prior art reactors are designed such that most of the reaction heat is generated in a region of the reactor close to the gas inlet 1. This is so because when the reacting gas mixture is in this zone it may still be in the conditions it has been set to be, and which will usually have been chosen so as to optimize the reaction yield. However at this initial stage the reacting gas mixture has not been heated up by reaction heat yet. Therefore, as the oxidation of n-butane sets in, temperature starts increasing as a function of axial distance inside the reactor in the direction of flow of the reacting gas mixture. A typical spatial temperature profile, like the one shown in FIG. 2, continues to increase with distance inside the reactor in the direction of flow of the reacting gas mixture due to the fact that more reaction heat is being generated than the liquid coolant is able to dissipate. Eventually, a point is reached at which enough n-butane has reacted for the rates of reaction heat generation and of heat dissipation by the liquid coolant to equalize, such that the spatial temperature profile first flattens and then start dropping. The location at which the spatial temperature profile flattens corresponds to a point of maximum temperature inside the reactor, which is usually referred to as "hot spot". When conditions inside the reactor are under proper control, the hot spot is located in an intermediate region of the reactor along the way of the reacting gas mixture through it. From that point on, the temperature monotonically decreases towards the gas outlet, as seen in FIG. 2.

The location and the height, i.e. the temperature value, of the hot spot can have critical effects on the reactions taking place inside the reactor. If the hot spot temperature becomes too high, structural damage of the catalyst may occur, which leads to a significant reduction of the life-cycle thereof. This typically happens if the catalyst temperature exceeds a critical temperature of about 480° C. In addition, excessive catalyst degradation due to too high temperatures may cause the hot spot to migrate towards the end of the reactor, which makes it necessary to reduce the n-butane concentration or its flow velocity, for otherwise, the gases exiting the reactor may still contain enough unreacted n-butane to cause an explosion or fire.

Conventionally, a tubular reactor for maleic anhydride production comprises a big vessel that might be as high as 7 to 10 m and have a diameter of up to 6 m traversed by several thousand tubes (typically between 5000 and 30,000) in which the reactant gases are passed and are exposed to the catalyst contained inside the tubes. The heat transfer agent or coolant is then made to flow through the vessel over the outsides of the tubes. A length of the tubes is usually referred to as "catalyst bed".

In order to increase the reaction yield for reaction (1) to obtain more maleic anhydride, an increase in the throughput of n-butane entering the reactor may in principle be attempted. However, an increased n-butane throughput inevitably leads to more n-butane reacting according to the parallel reactions (2) to (5) as well, and hence to an increased generation of reaction heat, which results in a temperature increase inside the reactor. Further, higher temperatures tend to favour the oxidation of n-butane to $CO_2$ and water, which is a process more exothermic than the main reaction (1). Consequently, the temperature change caused by an increase in the throughput of n-butane may lead to a higher temperature of the hot spot and to a larger fraction of n-butane reacting according to reactions (2) to (5), thereby giving rise to a smaller yield of maleic anydride.

This effect may be partly compensated by means of the catalyst activity, that is, the degree to which the catalyst accelerates the above reactions. A mixture of catalyst and an inert solid may be used to effectively dilute the catalyst in a controlled manner. Varying this mixture allows the rate of reaction in different parts of the catalyst bed to be controlled in such a way that the reduced selectivity caused by the increase in temperature can be appropriately compensated by an increased conversion rate. For example, the catalyst may be chosen to have a relatively low activity in the region where the hot spot occurs so as to minimize the magnitude thereof.

Examples of the spatial distribution of the estimated catalyst temperature along the catalyst bed, that is, as a function of height from a bottom tubesheet of the reactor, in a single reaction zone reactor are shown in FIG. 2. The direction of flow of the reacting gas mixture is represented as being from left to right. The square symbols show a case in which, as described above, the temperature starts increasing as the oxidation reaction sets on until a point of maximum temperature, the hot spot, is reached, which in the first case corresponds to a height over the bottom tubesheet of about 1400 mm and to a temperature of 450° C. The diamond symbols represent a case in which the temperature of the liquid coolant is higher than in the case corresponding to the square symbols. It can be seen that an increase in the temperature of the liquid coolant results in a higher temperature of the hot spot (around 460° C.). The change is however not significant in the higher regions of the reactor. The triangular symbols represent a case in which the catalyst is mixed with a larger amount of trimethyl phosphate than in the case represented by the square symbols. In this case, the maximum temperature, i.e. the hot spot temperature, is reduced to below 450° C. and a more gradual temperature increase in the lower part of the reactor is observed, while again, the temperature in the higher part of the reactor is hardly influenced by the modification of the catalyst.

An alternative approach was suggested in Wellauer et al., Chem.ng. Sci. Vol. 41, No. 4 (1986) pp. 765-772, according to which the process of preparing maleic anhydride is optimised by influencing the activity of the reactions through the temperature of the coolant used to dissipate the reaction heat. This was achieved by dividing the reactor into two catalyst beds or reaction zones and by independently setting two different coolant temperatures respectively. However, this alternative method did not achieve a significant increase in the reaction yield compared to the case of a reactor using a single catalyst bed and a single coolant temperature.

The method was further developed in U.S. Pat. No. 6,803,473 B2, where a process for preparing maleic anhydride in a reactor having at least two successive reaction zones cooled by independent circuits of heat transfer media or coolants is disclosed. Herein, a "reaction zone" refers to a region within the reactor in which a catalyst is kept at a controlled temperature. The temperature inside the reactor can hence be set independently in each of the reaction zones. In this part of the reactor, the temperature in the first reaction zone in the flow direction is preferably between 380° C. and 430° C., whereas the temperature in the second and further reaction zones in the flow is in a preferred range from 350° C. to 480° C., wherein the temperature difference between the hottest reaction zone and the coolest reaction zone is in any case at least 2° C. In general, the temperature is described to increase from zone to zone in the flow direction of the reacting gas mixture.

The inventors of U.S. Pat. No. 6,803,473 B2 emphasise that the yield of maleic anhydride significantly depends on the temperature difference between the hot spot maximum established in the different reaction zones, and in particular that the yield of maleic anhydride increases with increasing temperature difference between the hot spot maximum of the second or subsequent reaction zones and the hot spot maximum of a preceding reaction zone. Accordingly, they presented a reactor design in which at least one hot spot maximum of the second or subsequent reaction zones is higher than all hot spot maxima in preceding reaction zones, in particular higher than the hot spot temperature in the first reaction zone.

However, the aforementioned design has the drawback that the high temperature in the second reaction zone implies higher catalyst temperature and a larger magnitude of the hot spot therein, which negatively affects the length of the catalyst lifecycle and leads to a suboptimal reaction selectivity. In view of this, there is room for technical improvements in the design of a tubular reactor for maleic anhydride production.

SUMMARY OF THE INVENTION

The problem underlying the invention is to provide a reactor and a method for producing maleic anhydride by the oxidation of n-butane with optimized reaction conditions and an improved control of the spatial temperature profile and the maximal temperatures occurring inside the reactor in order to improve the reaction yield and the life-cycle of the catalysts employed in the reactor. This problem is solved by a tubular reactor for carrying out exothermic oxidation gaseous reactions to produce maleic anhydride from a gas mixture containing n-butane and oxygen according to claim 1 and a method according to claim 17. Preferred embodiments of the invention are defined in the dependent claims.

The tubular reactor of the invention comprises a first reaction zone comprising an inlet for the gas mixture and a second reaction zone comprising an outlet for reaction gas mixture containing maleic anhydride, wherein the first reaction zone precedes the second reaction zone in a direction of flow of the gas mixture. If the gas mixture flows e.g. vertically upwards through the reactor, the first reaction zone is hence positioned below the second reaction zone, whereas if the gas mixture flows e.g. vertically downwards through the reactor, the first reaction zone is positioned above the second reaction zone.

The reactor comprises a plurality of tubes extending in an axial direction through said first and second reaction zones, which are communicatively connected with said inlet and said outlet via respective first and second ends thereof. Hence each of the tubes extends through the first and the second reaction zones and has a first end communicatively connected with one of the inlet and the outlet and a second end communicatively connected with the other one of the inlet and the outlet, so that the gas mixture may flow through the tubes between the inlet and the outlet.

The reactor further comprises a temperature control system configured for controlling a reaction temperature in each of the reaction zones independently. The temperature control system comprises a heat transfer system for each of the reaction zones configured for controlling the temperature of the liquid coolant flowing through one of the reaction zones. In particular, the temperature control system may comprise a first heat transfer system and a second heat transfer system, wherein each of the heat transfer systems is configured for controlling temperature at which the liquid coolant enters the corresponding reaction zone for cooling purposes. In other words, the temperature control system may comprise a first heat transfer system for controlling the temperature of the liquid coolant flowing through the first reaction zone and a second heat transfer system for controlling the temperature of the liquid coolant flowing through the second reaction zone, wherein the reaction temperatures in the first reaction zone and in the second reaction zone can be controlled independently.

Note that although reference to "the reaction temperature in a reaction zone" is made, it is understood that the reaction temperature within each reaction zone may vary according to a corresponding spatial temperature profile. Still, according to the present invention at least the average reaction temperature in each reaction zone can be controlled independently. Moreover, the fact that the temperature control is independent does of course not mean that the temperatures as such are independent, since the temperature in the second reaction zone will certainly depend on the temperature in the first reaction zone and vice versa. Still the controls of the temperatures are independent from each other, as will become apparent from the specific embodiments described below.

A heat transfer system in the sense of the present invention generally refers to a heat exchanger of any kind suitable for absorbing the heat of the liquid coolant so as to cool it down to a preset temperature. In particular, the aforementioned heat transfer systems may take the form of heat exchangers through which the liquid coolant flows in thermal contact with a flow of water, such that the temperature of the liquid coolant may be controlled by changing the flow conditions or the temperature of the water flowing through the heat exchanger in thermal contact with the liquid coolant, for example by means of a valve control. Reducing the temperature of the liquid coolant circulating within one of the reaction zones has the effect of increasing the amount of reaction heat that the liquid coolant can absorb in this reaction zone, which results in a reduction of the temperature at which the reaction takes place in this reaction zone.

The temperature of the liquid coolant circulating within each of the reaction zones may be regulated by the corresponding heat transfer system. The liquid coolant is cooled back to a preset temperature at a corresponding heat transfer system between two circulation cycles in the reactor. In particular, the heat transfer system for the first reaction zone may be configured to cool down the liquid coolant to a first preset temperature while the transfer system for the second reaction zone may be configured to cool down the liquid coolant to a second preset temperature. The first and second preset temperatures need not be equal. Preferably, the first preset temperature is lower than the second preset temperature. This leads to a decrease in the reaction temperature in the first reaction zone and to an increase in the reaction temperature in the second reaction zone as compared to the case in which both preset temperatures are equal. Thereby, the n-butane conversion in the second reaction zone can be considerably increased, while an eventual temperature reduction in the first reaction zone does not imply a drastic reduction of the reaction efficiency in the first reaction zone due to the much higher n-butane and oxygen concentration in the first reaction zone.

The temperature control system further comprises a circulation pumping system configured for controlling flow conditions of the liquid coolant flowing through the reactor and through the heat transfer systems. The pumping system drives a flow of the liquid coolant through the reactor. In particular, the liquid coolant flows through the reactor between the tubes inside which the oxidation reaction takes place, thereby absorbing the generated reaction heat upon warming up. The flow of the liquid "coolant" is also used for heating up the gas mixture inside the reactor upon start-up of the reactor to a desired reaction temperature so as to initiate the oxidation reaction as well as for removing reaction heat generated inside the reactor during the operation thereof. The pumping system further drives a flow of the liquid coolant through the heat transfer systems, at which the liquid coolant is cooled down back to the corresponding preset temperature and then circulated back into the reactor. The cooling down may take place in one of the heat transfer systems by using the liquid coolant to heat up and boil water to generate steam.

The reactor further comprises a preheating arrangement configured for preheating the gas mixture such that the gas mixture enters the first reaction zone at a predefined inlet temperature. A "heating arrangement" refers herein to any arrangement or device suitable for controlling the temperature of gas or gas mixture entering the reactor and setting it to a predefined value. For example, the heating arrangement may comprise a feed gas preheater operated with steam produced in one or more of the heat transfer systems. Such a feed gas preheater may comprise a heat exchanger that uses the condensation heat of said steam for warming up the gas mixture entering the reactor to the predefined inlet temperature.

In the reactor of the invention, the oxidation reaction does not predominantly take place concentrated in one region of the reactor only, as is the case in traditional reactors. Instead, the independent temperature control in different reaction zones allows creating the conditions for the reaction to concentrate in a second reaction zone as well, which is located further along the axial length of the reactor. Thereby, the reaction is better distributed along the reactor, i.e. along the tubes, which allows for an improved reaction yield.

The reactor of the invention is characterised in that the axial length of the tubes within the first reaction zone corresponds to between 30% and 45% of the total length covered by the tubes within the first and second reaction zones, under the proviso that the inlet temperature and the proportions of the length of the tubes arranged in the first and second reaction zones are such that a total heat generated by the exothermic reactions inside the first reaction zone is equal or larger than an amount of heat required for preheating the gas mixture to the predefined inlet temperature.

The inventors of the present invention have realised a way of designing a reactor in such a manner that the efficiency of the production of maleic anhydride, which is mostly given by the reaction yield, can be kept high or even be increased, while the length of the life-cycle of the catalysts employed in the reactor is improved. The invention is based on concrete design specifications of a tubular reactor having two reaction zones cooled by independent circuits of heat transfer media or coolants, as is per se known from the prior art cited above. However, the present invention notably deviates from previously known solutions by suggesting concrete design specifications of the reactor based on an unequal length of the two reaction zones. The invention inventors have found out that this choice of relative axial lengths of the reaction zones play a crucial role in increasing the reaction yield and at the same time preventing excessive reaction temperatures so as to increase the life-cycle of the catalyst.

A key aspect of the present invention is the delicate balance between the relative size of the reaction zones, which is determined by the part of the axial length of the tubes comprised within each of the reaction zones, and the inlet temperature at which the gas mixture enters the reactor. According to the invention, the axial length of the tubes within the first reaction zone corresponds to between 30% and 45% of the total length covered by the tubes within the first and second reaction zones. This reflects an upper bound in the relative size of the first reaction zone with respect to the second reaction zone. With reference to previously known solutions in which both reaction zones are equal in size, the first reaction zone is made smaller in the present invention so that a smaller part of the reacting n-butane reacts in the first reaction zone and instead enters the second reaction zone to react therein. Thereby, the n-butane an oxygen concentration in the second reaction zone is increased with respect to previously known solutions.

Further, the inventors have realised that the upper bound in the relative size of the first reaction zone with respect the second reaction zone described above must be complemented by the proviso that the inlet temperature and the proportions of the length of the tubes arranged in the first and second reaction zones are such that a total heat generated by the exothermic reactions inside the first reaction zone is equal or larger than an amount of heat required for preheating the gas mixture to the predefined inlet temperature. This way, it is ensured that the total reaction heat generated in the first reaction zone is higher than the heat required for preheating the cold gas mixture to the predefined inlet temperature, which helps maintaining stable temperature control in the first reaction zone.

Hence the invention provides an improved reactor design based on appropriate bounds to the relative size of the two reaction zones with respect to each other and to the predefined inlet temperature in order to control the magnitude and the location of the hot spots inside the first and second reaction zones in such a way that the reaction yield of n-butane oxidation be optimized while maximizing the life-cycle length of the catalyst present in the reactor. The reactor of the invention achieves a more uniform temperature distribution within the reactor, with a high average temperature, but with decreased hot spot temperature as compared to previously known reactors, thereby allowing for an increased life-cycle of the catalyst. Further, the independent control of the flow conditions of the liquid coolant in the first reaction zone and in the second reaction zone provides additional control possibilities over the conditions in which the oxidation reaction takes place in each of the zones, thereby allowing for reduced impact of the conditions set in one reaction zone on the conditions set in the other reaction zone.

In a preferred embodiment of the invention the axial length of the tubes within the first reaction zone, and the settings of the preheating arrangement, the circulation pumping system, and the heat transfer systems are chosen such that a maximum value of the reaction temperature in the first reaction zone is equal or larger than a maximum value of the reaction temperature in the second reaction zone. Thereby, all configurable parameters of the reactor of the invention are chosen such that the aforesaid condition is fulfilled. "Setting" refers herein to the choice of any possible parameter related to the working conditions of the preheating arrangement, the circulation pumping system and the heat transfer systems and through which the conditions under which the gas mixture reacts inside the reactor may be influenced. In particular, said parameters may comprise a target temperature of the preheating arrangement, flow conditions of the liquid coolant induced by the circulation pumping system and a temperature to which the liquid coolant is cooled down at a heat transfer system.

Further, the reactor of the invention may comprise a control unit operatively connected to the temperature control system, i.e. to one or more of the heat transfer systems, the circulation pumping system and the preheating arrangement and configured for controlling their settings according to the aforementioned parameter choice. Thereby a further bound is set that ensures that the spatial temperature profile is such that the reaction is distributed over the length of the reactor as uniformly as possible, in other words, that a part of the reacting n-butane reacting in the second zone is large enough for an optimal reaction yield to be achieved, while the temperature in the second reaction zone is kept well below a critical temperature that would lead to a significant reduction of the catalyst life-cycle.

According to preferred embodiments of the invention, the inlet temperature is in a range between 150° C. and 250° C., preferably between 175° C. and 225° C. The value of the inlet temperature depends on the length of the first reaction zone. In particular, a shorter first reaction zone may require the use of a higher value of the inlet temperature.

In a preferred embodiment of the invention the temperature control system comprises a circulation pumping system for each of the reaction zones configured for controlling the flow conditions of the liquid coolant flowing within each of the reaction zones independently. This allows controlling the flow conditions of the liquid coolant in the first reaction zone and in the second reaction zone independently. Thereby, a better control of the reaction heat absorbed in each of the reaction zones is provided. One or both of the aforesaid circulation pumping systems may be installed within the reactor, preferably in a vertical centrifugal pumping system located at the center of the reactor, e.g. inside a hole of a reactor. At least one of the aforesaid circulation pumping systems or both circulation pumping systems may be comprised in a vertical centrifugal pumping system located at the center of the reactor. However, both circulation pumping systems may be comprised in a vertical centrifugal pumping system located outside of the reactor. A "circulation pumping system" refers herein to any system or device suitable for driving a circulating liquid flow. In particular, a circulation pumping system may comprise a vertically positioned pump and/or an impeller pushing the liquid coolant downwards. The flow conditions of the liquid coolant, like the velocity thereof, may then be varied by modifying the rotating speed of said impeller, for example by means of a frequency inverter.

Having both of the circulation pumping systems installed in a central part of the reactor further results in a more homogeneous circulation of the liquid coolant through the reaction zones, in which the gas carrying tubes are located and hence to a better temperature control.

According to preferred embodiments of the invention, at least one of the heat transfer systems is located inside the reactor, preferably in the central part of the reactor. Preferably, each heat transfer system is located next to a circulation pumping system in order to allow for a better control of the flowing conditions of the liquid coolant inside the heat transfer system. Hence, in embodiments having both circulation pumping systems installed in a central part of the reactor, both heat transfer systems are preferably located in said central part of the reactor as well, respectively located next to a circulation pumping system. In embodiments having one or both circulation pumping systems installed outside of the reactor, corresponding heat transfer systems may be located outside of the reactor next to the circulation pumping systems. In another preferred embodiment of the invention, both heat transfer systems may be located outside the reactor.

In a preferred embodiment of the invention, the liquid coolant flows in the same direction as the gas mixture within at least one of the reaction zones, preferably within the first reaction zone. Further, the liquid coolant may flow in the opposite direction as the gas mixture within at least one of the reaction zones, preferably within the second reaction zone. Accordingly, the liquid coolant may flow in each of the reaction zones in the same direction as the gas mixture or in the opposite direction. For example, the liquid coolant flow may flow in the same direction as the gas mixture in the first reaction zone and in the second reaction zone. Further, the liquid coolant may flow in the same direction as the gas mixture within the first reaction zone, while the liquid coolant flows in the opposite direction as the gas mixture within the second reaction zone. This has the advantage that the reaction gas exiting the reactor may have a lower temperature, which diminishes the chances of unwanted post-reactions taking place around the reactor outlet.

In a preferred embodiment of the invention, the liquid coolant flows within at least one reaction zone at a flowing velocity that decreases along the direction of flow of the gas mixture. This may be achieved by a plurality of baffles installed inside the reactor and configured for directing a meandering flow of the liquid coolant through the reactor, wherein an axial distance between pairs of adjacent baffles increases along the direction of flow of the gas mixture within said at least one reaction zone. This configuration may extend to both reaction zones.

Since the liquid coolant circulates between the baffles along the radial direction of the reactor in an alternating outwards and inwards flow, the distance between two successive baffles determines the effective cross-sectional area of the flow of the liquid coolant, which has direct influence upon the fluid velocity. A larger distance implies a larger cross-sectional area and hence a slower flowing liquid coolant. A faster flowing liquid coolant heats up less than a slowing flowing liquid coolant covering the same distance within the reactor, such that a faster flowing liquid coolant provides a more efficient cooling effect. Thus, when the flowing velocity of the liquid coolant decreases along the direction of flow of the gas mixture within a reaction zone, the temperature inside said reaction zone will be reduced in an initial sub-zone of said reaction zone and increased in a final sub-zone of said reaction zone, as compared to the case of a uniform flow with the same average flow velocity, an initial sub-zone being located downstream with respect to a final sub-zone by reference to the flow of the liquid coolant.

Alternatively or additionally, the liquid coolant may flow in preferred embodiments of the invention within at least one reaction zone at a flowing velocity that increases along the direction of flow of the gas mixture. In that case, the reactor preferably further comprises a plurality of baffles installed inside the reactor and configured for directing a meandering flow of the liquid coolant through the reactor, wherein an axial distance between pairs of adjacent baffles decreases along the direction of flow of the gas mixture within said at least one of the reaction zones. In this case, the temperature inside said reaction zone will be increased in an initial sub-zone of said reaction zone and reduced in a final sub-zone of said reaction zone, an initial sub-zone being located downstream with respect to a final sub-zone by reference to the flow of the liquid coolant. This configuration may extend to both reaction zones or may be combined with the alternative configuration described above.

Another aspect of the invention relates to a method of carrying out exothermic oxidation gaseous reactions to produce maleic anhydride from a gas mixture containing n-butane and oxygen in a tubular reaction according to any of the embodiments described above comprising: a first reaction zone having an inlet for said gas mixture and a second reaction zone having an outlet for reaction gas mixture containing maleic anhydride, wherein the first reaction zone precedes the second reaction zone in a direction of flow of the gas mixture, a plurality of tubes extending in an axial direction through said first and second reaction zones and communicatively connected with said inlet and said outlet with respective first and second ends thereof; a temperature control system for controlling a reaction temperature in each of the reaction zones independently, wherein the temperature control system comprises a heat transfer system for each of the reaction zones configured for controlling a reaction temperature in each of the reaction zones independently and a circulation pumping system configured for controlling flow conditions of a liquid coolant flowing through the reactor and through the heat transfer system; and a preheating arrangement configured for preheating the gas mixture such that the gas mixture enters the first reaction zone at a predefined inlet temperature; wherein the axial length of the tubes within said first reaction zone corresponds to between 30% and 45%.

The method of the invention comprises the steps of:
setting the temperature of a liquid coolant flowing through the reactor in each of the reaction zones independently by means of the heat transfer systems;
setting the flow conditions of the liquid coolant by means of the circulation pumping system;
preheating the gas mixture such that the gas mixture enters the reactor at a predefined inlet temperature by means of the preheating arrangement; and setting the inlet temperature a total heat generated by the exothermic reaction inside the first reaction zone is equal or larger than an amount of heat required for preheating the gas mixture to the predefined inlet temperature.

According to a preferred embodiment of the invention the method further comprises setting the preheating arrangement, the heat transfer systems and the circulation pumping system such that a maximum value of the reaction temperature in the first reaction zone is equal or larger than a maximum value of the reaction temperature in the second reaction zone Thereby, all configurable functions of the reactor of the invention may be chosen such that the aforesaid condition is fulfilled. "Setting" refers herein to any possible action that may be carried out using the preheating arrangement, the circulation pumping system and the heat transfer systems with the purpose of influencing the conditions under which the gas mixture reacts inside the reactor. In particular, "setting" may refer to setting a target temperature of the breeding arrangement, to setting the flow conditions of the liquid coolant by means of the circulation pumping system and to setting a temperature to which the liquid coolant is called down at the heat transfer systems. The step of setting may be carried out by a control unit operatively connected to the corresponding components of the reactor.

In a preferred embodiment of the invention the inlet temperature is set in a range between 150° C. and 250° C., preferably between 175° C. and 225° C.

According to a preferred embodiment of the invention the temperature control system of the reactor comprises a circulation pumping system for each of the reaction zones configured for controlling the flow conditions of the liquid coolant in each of the reaction zones independently, and wherein the method further comprises a step of setting the flow conditions of the liquid coolant in each of the reaction zones independently by means of the circulation pumping systems.

In a preferred embodiment of the invention the liquid coolant comprises a molten eutectic salt mixture.

In a preferred embodiment of the invention the temperature of the liquid coolant is set between 380° C. and 450° C., preferably between 400° C. and 440° C.

According to a preferred embodiment of the invention the temperature of the liquid coolant in the first reaction zone is set to a lower value than the temperature of the liquid coolant in the second reaction zone.

DESCRIPTION OF THE PREFERRED EMBODIMENTS

Figure 1:
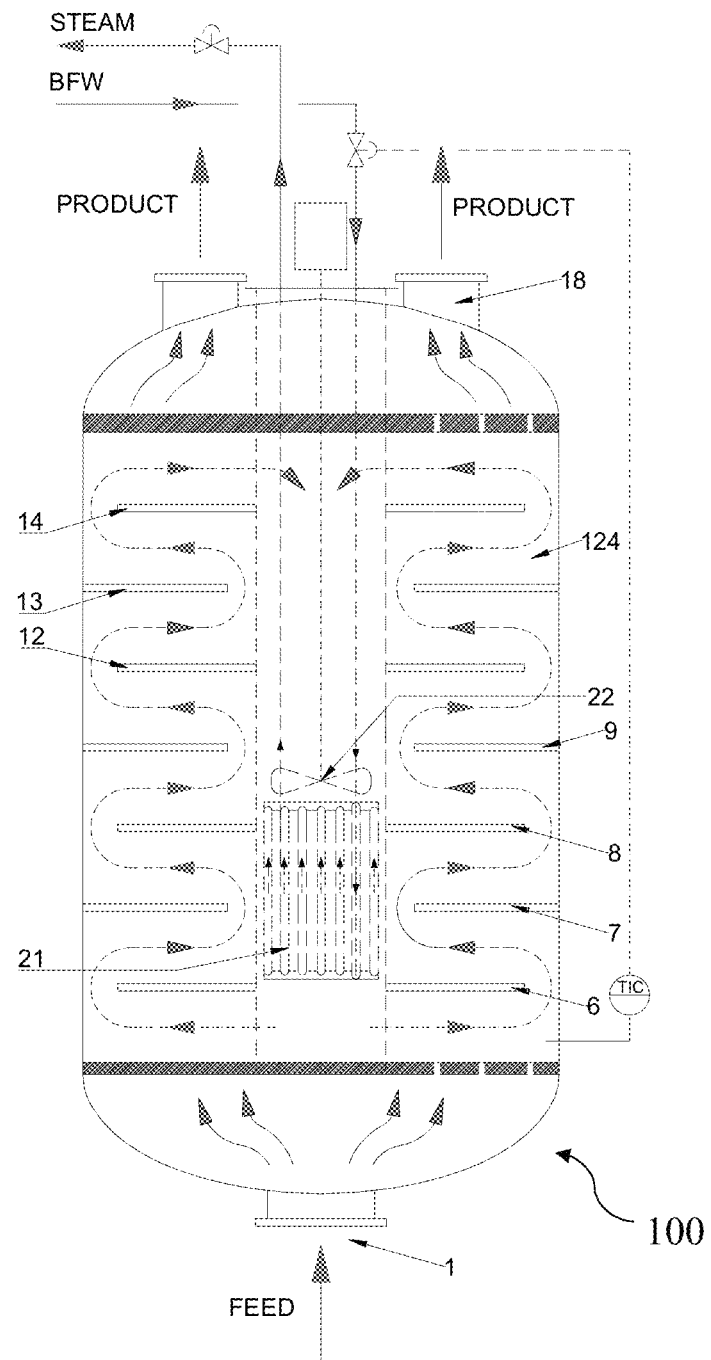
FIG. 1 shows a tubular reactor according to the prior art.
Figure 2:
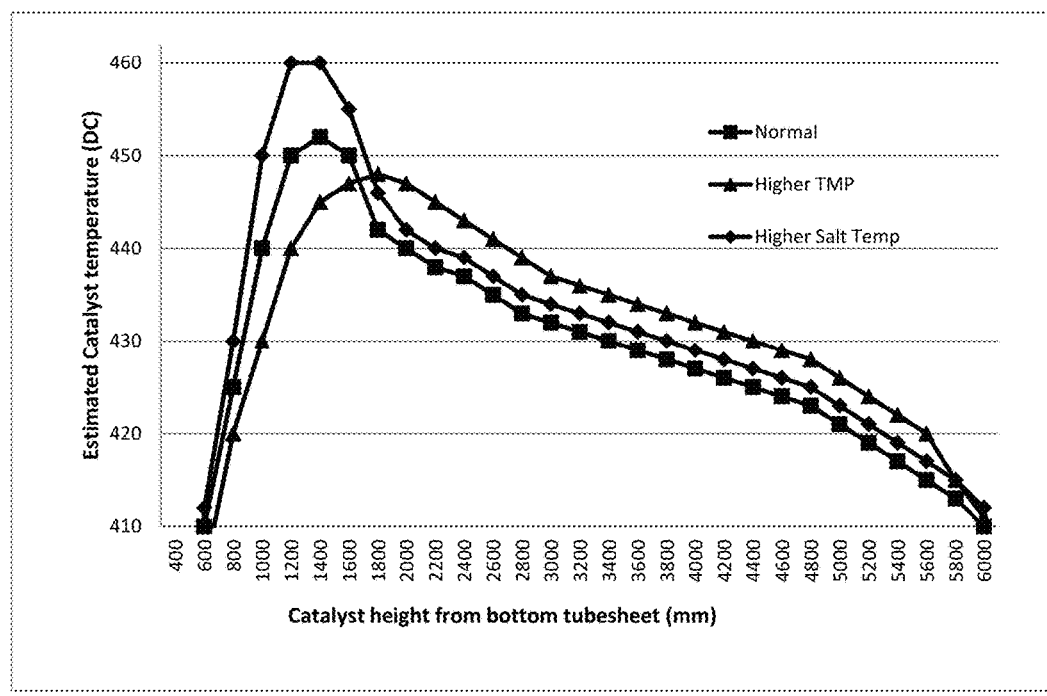
FIG. 2 shows an exemplary spatial temperature distributions obtained in tubular reactors known in the prior art.

For the purposes of promoting an understanding of the principles of the invention, reference will now be made to a preferred embodiment illustrated in the drawings, and specific language will be used to describe the same. It will nevertheless be understood that no limitation of the scope of the invention is thereby intended, such alterations and further modifications in the illustrated apparatus and such further applications of the principles of the invention as illustrated therein being contemplated as would normally occur now or in the future to one skilled in the art to which the invention relates.

Figure 3:
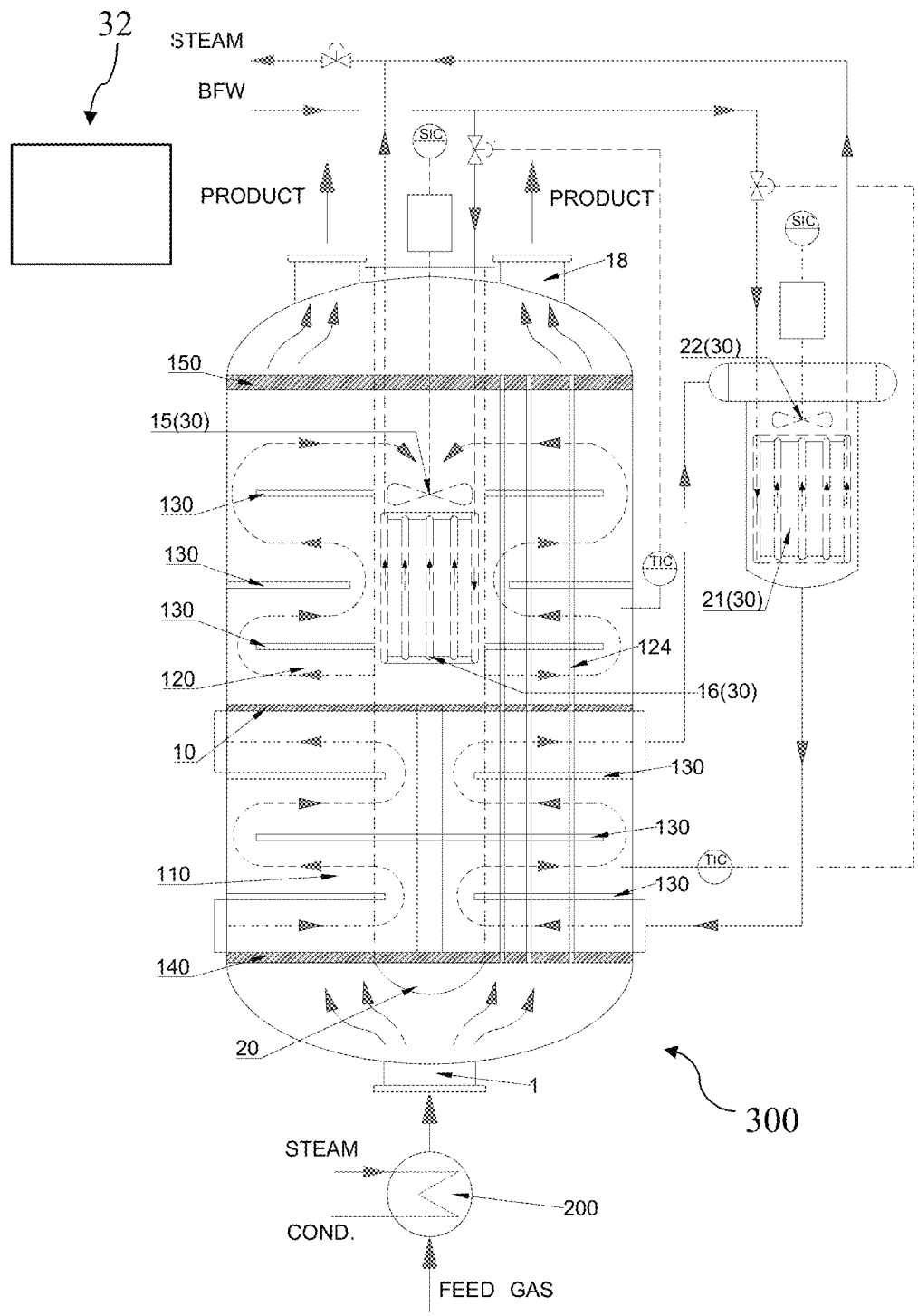
FIG. 3 shows a tubular reactor according to an embodiment of the invention.

FIG. 3 shows a tubular reactor 300 for carrying out exothermic oxidation gaseous reactions to produce maleic anhydride from a gas mixture containing n-butane and oxygen according to an embodiment of the invention. The tubular reactor 300 comprises a first reaction zone 110 comprising an inlet 1 for introducing the gas mixture into the reactor 300 and a second reaction zone 120 comprising an outlet 18 for reaction gas mixture containing maleic anhydride. The first reaction zone 110 precedes the second reaction zone in the direction of flow of the gas mixture, which in the figure corresponds to an upward vertical direction. The reactor 300 comprises a plurality of tubes 124 configured for being filled with a catalyst extending in the axial direction through the first and second reaction zones 110, 120, of which only a reduced number is exemplarily and schematically shown in the Figure. Each tube is communicatively connected to the inlet 1 and to the outlet 18 with respective first and second ends thereof.

The reactor 300 further comprises temperature control system 30 comprising a first heat transfer system 21 for the first reaction zone 110 configured for controlling a reaction temperature in the first reaction zone 110, and a second heat transfer system 16 configured for controlling a reaction temperature in the second reaction zone 120. The heat transfer systems 21 and 16 are respectively configured for controlling the reaction temperatures in the first and second reaction zones 120 and 110 independently. In the embodiment shown, the heat transfer systems 21 and 16 are heat exchangers in which the liquid coolant is put into thermal contact with a flow of cooling water. The cooling water absorbs part of the thermal energy stored in the liquid coolant thereby cooling the liquid coolant down and giving rise to an outflow of steam. The flow conditions of the cooling water and/or of the outflow of steam can be controlled in such a way that the amount of thermal energy absorbed by the cooling water is such that the liquid coolant be cooled down to a desired preset temperature. Since the heat transfer systems 21 and 16 work independently, i.e. the corresponding heat exchangers can be operated independently, the value of said preset temperature may be chosen differently for the first and second reaction zones 110 and 120.

The temperature control system 30 further comprises a first circulation pumping system 22 configured for controlling flow conditions of a liquid coolant flowing through the reactor 300 in the first reaction zone 110 and through the first heat transfer system 21 and a second circulation pumping system 15 configured for controlling flow conditions of the liquid coolant flowing through the reactor 300 in the second reaction zone 120 and through the second heat transfer system 16. In the embodiment shown, the heat transfer system 21 and the circulation pumping system 22 are located outside of the reactor 300. In the embodiment shown, a molten eutectic salt is used as liquid coolant. The circulation pumping system 22 is configured for driving the circulation of the liquid coolant to flow within the first reaction zone 110 in the same direction of flow of the gas mixture, that is, in the vertical upward direction. The heat transfer system 16 and the circulation pumping system 15 are comprised in a vertical centrifugal pumping system located inside the reactor 300, at the centre thereof. The circulation pumping system 15 is configured for driving the circulation of the liquid coolant to flow within the second reaction zone 120 in the same direction of flow of the gas mixture, that is, in the vertical upward direction.

Figure 5:
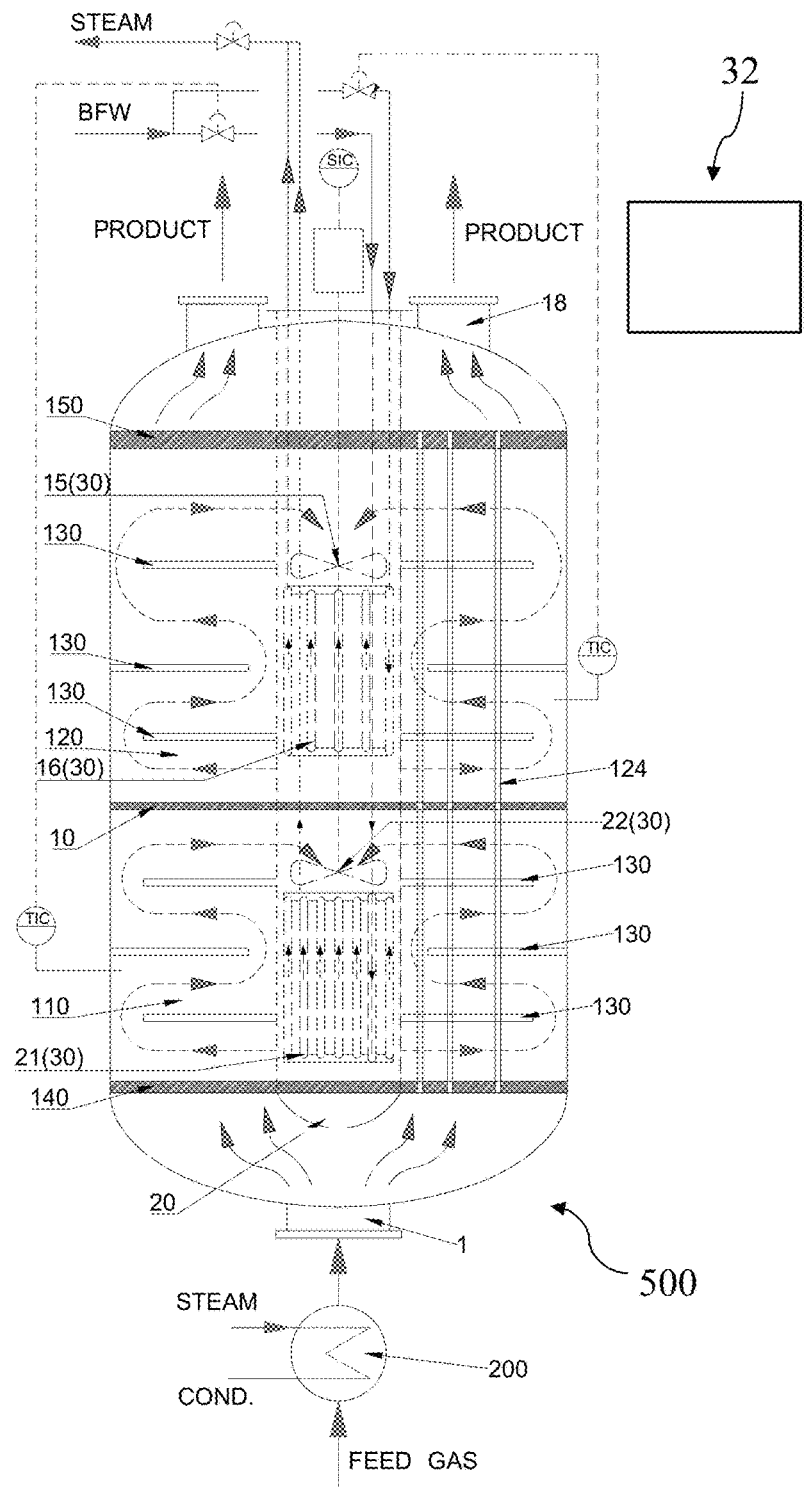
FIG. 5 shows a tubular reactor according to another embodiment of the invention.
Figure 6:
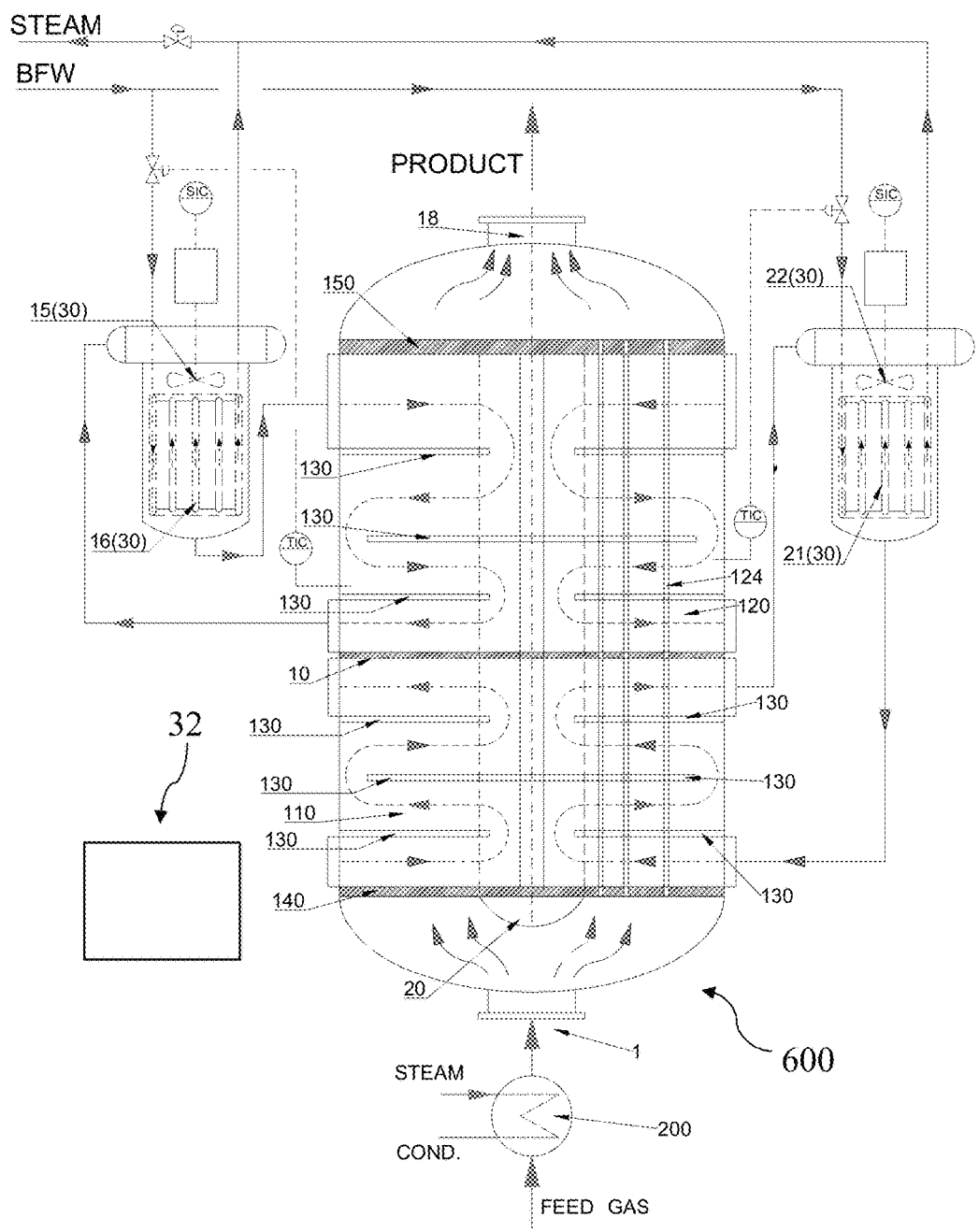
FIG. 6 shows a tubular reactor according to another embodiment of the invention.

The temperature control system 30 comprises the heat transfer systems 15 and 21, and the circulation pumping systems 16 and 22. This is indicated in FIGS. 3, 5, and 6 by a reference sign 30 shown in brackets next to the corresponding reference signs 15, 16, 21, and 22.

In the embodiment shown, the temperature control system 30 is operatively connected to a control unit 32, which is configured for controlling the operating conditions of the temperature control system 30, i.e. of the heat transfer systems 15 and 21 and of the circulation pumping systems 16 and 22. The control unit 32 is operatively connected to the heat transfer systems 15 and 21 and to the circulation pumping systems 16 and 22. Further, the control unit 32 may be operatively connected to the valves controlling the flow conditions of the liquid coolant, water and water steam in the heat transfer systems 15 and 21 and in the circulation pumping systems 16 and 22. Said connections may comprise connecting wires, wireless connections, or any other kind of operative connection. The connections are not shown in the figures for illustrative simplicity.

The existence of a second reaction zone 120 allows setting the conditions at which the oxidation reaction of n-butane continues to take place after the gas mixture has flown through the first reaction zone 110 by appropriately adjusting the temperature and the flow conditions of the liquid coolant entering the second reaction zone 120. Thereby, the oxidation reaction can be boosted, which results in a second boost of the production of reaction heat and hence in an increase in the catalyst temperature, as seen in the figure. This leads to an increase reaction yield but, in cases in which the hot spot temperature reached in the second reaction zone 120 becomes too high, the catalyst may start degrading and hence suffer from a reduced life cycle.

Therefore, in the reactor 300 shown in FIG. 3, the axial length of the tubes 124 through which the gas mixture flows in contact with a catalyst comprised within the first reaction zone 110 corresponds to between 30% and 45% of the total length covered by the tubes 124 within the first and second reaction zones 110 and 120. In the embodiment shown, the overall length of the tubes 124 amounts to 6 m and a separator plate 10 separating the first reaction zone 110 from the second reaction zone 120 is located at a position such that 2 m of the tubes 124 are comprised within the first reaction zone 110 and the remaining 4 m of the tubes 124 are comprised within the second reaction zone 120. A separator plate 10 may be any kind of device suitable for establishing a spatial separation between the two zones of the reactor. In the embodiment shown, the separator plate 10 of the present embodiment is a horizontally inserted plate having a size and geometry corresponding to an axial cross-section of the reactor 300. The separator plate 10 of the present embodiment comprises holes through which the tubes 124 of the reactor can traverse the separator plate 10. The separator plate 10 is not completely tight and allows a small exchange of coolant liquid between the first reaction zone 110 and the second reaction zone 120 such as to allow for a pressure exchange between the first and second reaction zones 110, 120.

The reactor 300 of FIG. 3 further comprises a plurality of baffles 130 installed inside the reactor 300 and configured for directing a meandering flow of the liquid coolant through the reactor 300. An axial distance between pairs of baffles 130 decreases along the direction of flow of the gas mixture within the first and second reaction zones 110 and 120, which in the embodiment shown corresponds to the upward vertical direction. This makes the liquid coolant flow within the first and second reaction zones 110 and 120 at a flowing velocity that increases along the direction of flow of the gas mixture. The number of baffles can vary, for example according to total length of the catalyst tubes 124.

Herein, the distance between the separator plate 10 separating said first and second reaction 110 and 120 zones and an adjacent baffle 130 and/or between one of a bottom tubesheet 140 and a top tubesheet 150 of the reactor and an adjacent baffle 130 are considered to be equivalent to the aforementioned "distance between adjacent baffles" for the purposes of this definition, since the separator plate 10, the bottom tubesheet 140 and the top tubesheet 150 guide the flow of the liquid eutectic salt in the same way as the baffles 130. The bottom tubesheet 140 and the top tubesheet 150 are respectively the lowermost and the uppermost surface of the reactor transversal to the tubes 124, i.e. transversal to the direction of flow of the gas mixture.

The reactor 300 of FIG. 3 further comprises a preheating arrangement 200 configured for preheating the gas mixture such that the gas mixture enters the first reaction zone 110 through the inlet 1 at a predefined inlet temperature $T_{in}$. The predefined inlet temperature $T_{in}$ is such that a total heat generated by the exothermic reactions inside the first reaction zone 110 is equal or larger than an amount of heat required for preheating the gas mixture to the predefined inlet temperature $T_{in}$ at the preheater 200. In the embodiment shown, the inlet temperature $T_{in}$ is a temperature in a range between 175° C. and 225° C.

The reactor 300 further comprises a deflector 20 located in a central lower part of the reactor below a lowermost portion of the tubes 124 and is configured for equalizing the flow of the gas mixture entering the reactor 300.

In the embodiment shown in FIG. 3, the liquid coolant is circulated by the first circulation pumping system 22 within the first reaction zone 110 in the same direction of flow as the gas mixture and further through the first heat transfer system 21, where the circulated liquid coolant is cooled back to a first preset temperature before being pumped back into the first reaction zone 110. Further, the liquid coolant is circulated by the second circulation pumping system 15 within the second reaction zone 120 in the same direction of flow as the gas mixture and through the second heat transfer system 16, where the circulated liquid coolant is cooled back to a second preset temperature before being pumped back into the second reaction zone 120. The surpluses of heat in the heat transfer systems 21 and 16 are removed by generating steam.

Figure 4:
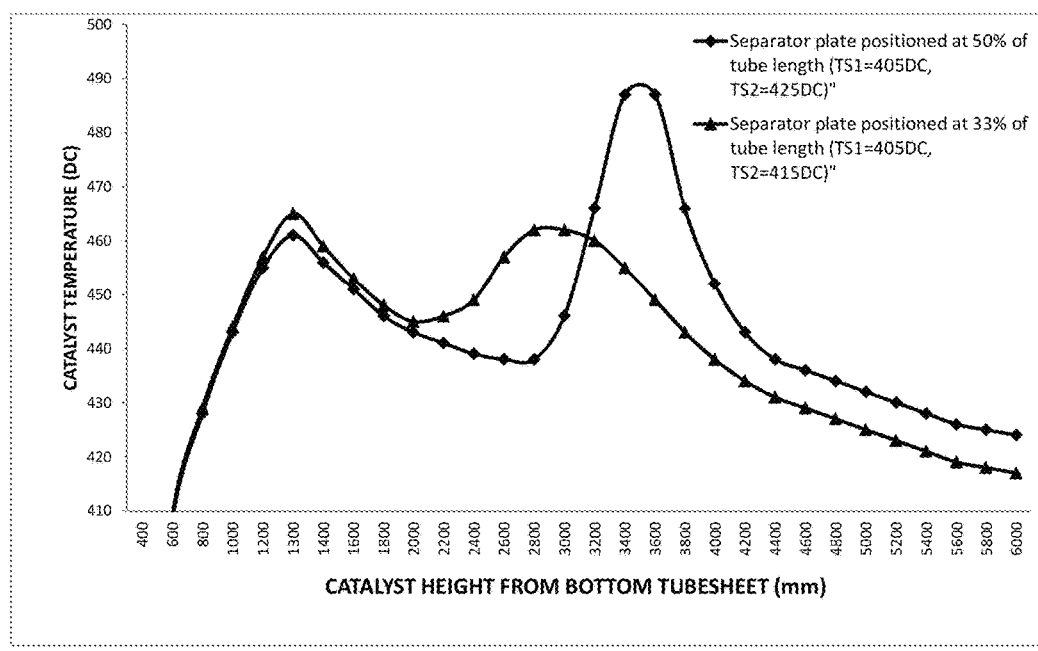
FIG. 4 shows an exemplary spatial temperature distribution obtained with a tubular reactor according to an embodiment of the invention.

The design specifications of the embodiment shown in FIG. 3 described above result in a spatial temperature distribution that is shown in FIG. 4. The diamond symbols stand for the case in which the first reaction zone and the second reaction zone have equal sizes, that is, the case in which the axial length of the tubes 124 within the first reaction zone corresponds to 50% of the total length covered by the tubes 124 within the first and the second reaction zones. The triangle symbols represent the case in which the volume of the first reaction zone is half the volume of the second reaction zone, that is, the case in which the axial length of the tubes 124 within the first reaction zone 110 corresponds to 33% of the total length covered by the tubes 124 within the first and second reaction zones 110 and 120.

As seen in FIG. 4, the reduction of the relative size of the first reaction zone implied by the condition that the axial length of the tubes 124 within the first reaction zone correspond to between 30% and 45% of the total length covered by the tubes 124 within the first and second reaction zones 110, 120 results in a slight increase of the reaction temperature in the first reaction zone 110—due to higher conversion rate and to a consequent higher temperature $TS_1$ of the liquid coolant in the first reaction zone—that is clearly balanced by a significant reduction of the reaction temperature in the second reaction zone 120—due to a lower temperature $TS_2$ of the liquid coolant in the second reaction zone. In the case in which the first reaction zone and the second reaction zone have equal sizes, signaled by the diamond symbols, the temperature of the liquid coolant in the first and second reaction zones is respectively 405° C. and 425° C. In the case in which the axial length of the tubes 124 within the first reaction zone 110 corresponds to 33% of the total length covered by the tubes 124 within the first and second reaction zones 110 and 120, signaled by the triangle symbols, the temperature of the liquid coolant in the first and second reaction zones is respectively 405° C. and 415° C. Thus, FIG. 4 is an example of how the relative reduction in the size of the first reaction zone 110 with respect to the second reaction zone 120 realised in the embodiment shown in FIG. 3 allows for a reduction of the temperature of the liquid coolant in the second reaction zone and results in a reduction of the maximum reaction temperature, i.e. the hot spot temperature, obtained in the second reaction zone 120. In the case shown in FIG. 4, the hot spot temperature in the second reaction zone 120 decreases from about 490° C. to about 460° C., which is below the critical degradation temperature for the catalyst of about 480° C.

Further, as seen in FIG. 4, the maximum value of the reaction temperature in the first reaction zone 110 is larger than the maximum value of the reaction temperature in the second reaction zone 120. In particular the hot spot temperature of the second reaction zone is notably reduced as compared to the case in which both reaction zones have equal sizes. The longer second reaction zone 120, i.e. the lower position of the separator plate 10, with respect to the case in which both reaction zones are equal in length, allows for a lower temperature $TS_2$ of the liquid coolant in the second reaction zone, which results in a significant reduction in the hot spot temperature therein and hence in an increased life-cycle of the catalyst. Further, the reaction is more uniformly and hence more efficiently distributed along the reaction tubes 124, which allows maintaining a higher maleic anhydride reaction yield. In addition, the hot spot temperature in the second reaction zone 120 is reduced, which allows for a longer catalyst life-cycle as compared to the case in which both reaction zones are equal in size.

FIG. 5 shows a tubular reactor 500 according to another embodiment of the invention comprising the same components as the tubular reactor 300 shown in FIG. 3, but in which both the first and the second heat transfer systems 16 and 21 and the first and second circulation pumping systems 15 and 22 are located inside the reactor 500 in a central part thereof.

FIG. 6 shows a tubular reactor 600 according to another embodiment of the invention comprising the same components as to tubular reactors 300 and 500 respectively shown in FIGS. 3 and 5, but in which both the first and a second heat transfer systems 16 and 21 and the first and second circulation pumping systems 15 and 22 are located outside the reactor 600. Further, the liquid coolant flows in the same direction as the gas mixture within the first reaction zone 110, which in the embodiment shown corresponds to the upward vertical direction, while the liquid coolant flows in the opposite direction as the gas mixture within the second reaction zone 120, which in the embodiment shown corresponds to the downward vertical direction.

Although the above embodiments have been described and illustrated in the figures referring to the gas mixture flowing in a upward vertical direction, it is clear to the skilled person that embodiments in which the tubular reactor of the invention is inverted with respect to the embodiments shown in the figures such that the gas mixture flows in a downward vertical direction are also disclosed herein.

Although preferred exemplary embodiments are shown and specified in detail in the drawings and the preceding specification, these should be viewed as purely exemplary and not as limiting the invention. It is noted in this regard that only the preferred exemplary embodiments are shown and specified, and all variations and modifications should be protected that presently or in the future lie within the scope of protection of the invention as defined in the claims.

The invention claimed is:

1. A tubular reactor for carrying out exothermic oxidation gaseous reactions to produce maleic anhydride from a gas mixture containing n-butane and oxygen comprising:
a first reaction zone comprising an inlet for said gas mixture and a second reaction zone comprising an outlet for a reaction gas mixture containing maleic anhydride, wherein the first reaction zone precedes the second reaction zone in a direction of flow of the gas mixture,
a plurality of tubes extending in an axial direction through said first and second reaction zones and communicatively connected with said inlet and said outlet with respective first and second ends thereof;
a temperature control system configured for controlling a reaction temperature in each of the reaction zones independently, wherein the temperature control system comprises:
a heat transfer system for each of the reaction zones configured for controlling the temperature of a liquid coolant flowing through one of the reaction zones; and;
a circulation pumping system configured for controlling flow conditions of the liquid coolant flowing through the reactor and through one of the heat transfer systems; and
a preheating arrangement configured for preheating the gas mixture such that the gas mixture enters the first reaction zone at a predefined inlet temperature;
wherein the axial length of the tubes within said first reaction zone corresponds to between 30% and 45% of the total length covered by the tubes within said first and second reaction zones; under the proviso that the inlet temperature and the proportions of the length of the tubes arranged in said first and second reaction zones are such that a total heat generated by the exothermic reactions inside the first reaction zone is equal or larger than an amount of heat required for preheating the gas mixture to the predefined inlet temperature, and wherein the liquid coolant flows within at least one reaction zone at a flowing velocity that decreases along the direction of flow of the gas mixture.

2. The tubular reactor of claim 1, wherein the axial length of the tubes within the first reaction zone and the settings of the preheating arrangement, the heat transfer systems and the circulation pumping system are chosen such that a maximum value of the reaction temperature in the first reaction zone is equal or larger than a maximum value of the reaction temperature in the second reaction zone.

3. The tubular reactor of claim 1, wherein the inlet temperature is in a range between 150° C. and 250° C.

4. The tubular reactor of claim 1, wherein the inlet temperature is in a range between 175° C. and 225° C.

5. The tubular reactor of claim 1, wherein the temperature control system comprises a circulation pumping system for each of the reaction zones configured for controlling the flow conditions of the liquid coolant flowing through one of the reaction zones and one of the heat transfer systems independently from the other one of the reaction zones and the other one of the heat transfer systems.

6. The tubular reactor of claim 5, wherein said at least one of the circulation pumping systems is comprised in a vertical centrifugal pumping system located at the center of the reactor.

7. The tubular reactor of claim 5, wherein both circulation pumping systems are comprised in a vertical centrifugal pumping system located at the center of the reactor.

8. The tubular reactor of claim 5, wherein both circulation pumping systems are comprised in a vertical centrifugal pumping system located outside of the reactor.

9. The tubular reactor of claim 1, wherein at least one of the heat transfer systems is located inside the reactor.

10. The tubular reactor of claim 1, wherein both heat transfer systems are located outside the reactor.

11. The tubular reactor of claim 1, wherein the liquid coolant flows in the same direction as the gas mixture within the first reaction zone.

12. The tubular reactor of claim 1, wherein the liquid coolant flows in the opposite direction as the gas mixture within the second reaction zone.

13. The tubular reactor of claim 1, wherein the reactor further comprises a plurality of baffles installed inside the reactor and configured for directing a meandering flow of the liquid coolant through the reactor, wherein an axial distance between pairs of adjacent baffles increases along the direction of flow of the gas mixture within said at least one reaction zone.

14. A tubular reactor for carrying out exothermic oxidation gaseous reactions to produce maleic anhydride from a gas mixture containing n-butane and oxygen comprising:
a first reaction zone comprising an inlet for said gas mixture and a second reaction zone comprising an outlet for a reaction gas mixture containing maleic anhydride, wherein the first reaction zone precedes the second reaction zone in a direction of flow of the gas mixture,
a plurality of tubes extending in an axial direction through said first and second reaction zones and communicatively connected with said inlet and said outlet with respective first and second ends thereof;
a temperature control system configured for controlling a reaction temperature in each of the reaction zones independently, wherein the temperature control system comprises:
a heat transfer system for each of the reaction zones configured for controlling the temperature of a liquid coolant flowing through one of the reaction zones; and;
a circulation pumping system configured for controlling flow conditions of the liquid coolant flowing through the reactor and through one of the heat transfer systems; and a preheating arrangement configured for preheating the gas mixture such that the gas mixture enters the first reaction zone at a predefined inlet temperature;
wherein the axial length of the tubes within said first reaction zone corresponds to between 30% and 45% of the total length covered by the tubes within said first and second reaction zones; under the proviso that the inlet temperature and the proportions of the length of the tubes arranged in said first and second reaction zones are such that a total heat generated by the exothermic reactions inside the first reaction zone is equal or larger than an amount of heat required for preheating the gas mixture to the predefined inlet temperature, wherein the liquid coolant flows within at least one reaction zone at a flowing velocity that increases along the direction of flow of the gas mixture.

15. The tubular reactor of claim 14, wherein the reactor further comprises a plurality of baffles installed inside the reactor and configured for directing a meandering flow of the liquid coolant through the reactor, wherein an axial distance between pairs of adjacent baffles decreases along the direction of flow of the gas mixture within said at least one reaction zone.

16. The tubular reactor of claim 14, wherein the axial length of the tubes within the first reaction zone and the settings of the preheating arrangement, the heat transfer systems and the circulation pumping system are chosen such that a maximum value of the reaction temperature in the first reaction zone is equal or larger than a maximum value of the reaction temperature in the second reaction zone.

17. The tubular reactor of claim 14, wherein the inlet temperature is in a range between 175° C. and 225° C.

18. The tubular reactor of claim 14, wherein the temperature control system comprises a circulation pumping system for each of the reaction zones configured for controlling the flow conditions of the liquid coolant flowing through one of the reaction zones and one of the heat transfer systems independently from the other one of the reaction zones and the other one of the heat transfer systems.

19. The tubular reactor of claim 18, wherein said at least one of the circulation pumping systems is comprised in a vertical centrifugal pumping system located at the center of the reactor.

20. The tubular reactor of claim 18, wherein both circulation pumping systems are comprised in a vertical centrifugal pumping system located at the center of the reactor.

21. The tubular reactor of claim 18, wherein both circulation pumping systems are comprised in a vertical centrifugal pumping system located outside of the reactor.

22. The tubular reactor of claim 14, wherein the liquid coolant flows in the same direction as the gas mixture within the first reaction zone.

23. The tubular reactor of claim 14, wherein the liquid coolant flows in the opposite direction as the gas mixture within at least one of the reaction zones, preferably within the second reaction zone.

24. A method of carrying out exothermic oxidation gaseous reactions to produce maleic anhydride from a gas mixture containing n-butane and oxygen in a tubular reactor, said tubular reactor comprising:
a first reaction zone having an inlet for said gas mixture and a second reaction zone having an outlet for reaction gas mixture containing maleic anhydride, wherein the first reaction zone precedes the second reaction zone in a direction of flow of the gas mixture,
a plurality of tubes extending in an axial direction through said first and second reaction zones and communicatively connected with said inlet and said outlet with respective first and second ends thereof;

a temperature control system configured for controlling a reaction temperature in each of the reaction zones independently, wherein the temperature control system comprises:
 a heat transfer system for each of the reaction zones configured for controlling the temperature of a liquid coolant flowing through one of the reaction zones; and;
 a circulation pumping system configured for controlling flow conditions of the liquid coolant flowing through the reactor and through one of the heat transfer systems; and
a preheating arrangement configured for preheating the gas mixture such that the gas mixture enters the first reaction zone at a predefined inlet temperature;
wherein the axial length of the tubes within said first reaction zone corresponds to between 30% and 45% of the total length covered by the tubes within said first and second reaction zones; under the proviso that the inlet temperature and the proportions of the length of the tubes arranged in said first and second reaction zones are such that a total heat generated by the exothermic reactions inside the first reaction zone is equal or larger than an amount of heat required for preheating the gas mixture to the predefined inlet temperature, wherein the liquid coolant flows within at least one reaction zone at a flowing velocity that decreases along the direction of flow of the gas mixture;
wherein the method comprises the steps of:
 setting the temperature of a liquid coolant flowing through the reactor in each of the reaction zones independently by means of the heat transfer systems;
 setting the flow conditions of the liquid coolant by means of the circulation pumping system;
 preheating the gas mixture such that the gas mixture enters the reactor at a predefined inlet temperature by means of the preheating arrangement; and
 setting the inlet temperature such that a total heat generated by the exothermic reaction inside the first reaction zone is equal or larger than an amount of heat required for preheating the gas mixture to the predefined inlet temperature.

25. The method of claim 24, wherein the method further comprises setting the preheating arrangement, the heat transfer systems and the circulation pumping system such that a maximum value of the reaction temperature in the first reaction zone is equal or larger than a maximum value of the reaction temperature in the second reaction zone.

26. The method of claim 24, wherein the inlet temperature is set in a range between 150° C. and 250° C.

27. The method of claim 24, wherein the inlet temperature is set in a range between 175° C. and 225° C.

28. The method of claim 24, wherein the reactor comprises a circulation pumping system for each of the reaction zones configured for controlling the flow conditions of the liquid coolant in each of the reaction zones independently, and wherein the method further comprises a step of setting the flow conditions of the liquid coolant in each of the reaction zones independently by means of the circulation pumping systems.

29. The method of claim 24, wherein the liquid coolant comprises a molten eutectic salt mixture.

30. The method of claim 24, wherein the temperature of the liquid coolant is set between 380° C. and 450° C.

31. The method of claim 24, wherein the temperature of the liquid coolant is set between 400° C. and 440° C.

32. The method of claim 24, wherein the temperature of the liquid coolant in the first reaction zone is set to a lower value than the temperature of the liquid coolant in the second reaction zone.

33. The method of claim 24, wherein the reactor further comprises a plurality of baffles installed inside the reactor and configured for directing a meandering flow of the liquid coolant through the reactor, wherein an axial distance between pairs of adjacent baffles increases along the direction of flow of the gas mixture within said at least one reaction zone.

34. A method of carrying out exothermic oxidation gaseous reactions to produce maleic anhydride from a gas mixture containing n-butane and oxygen in a tubular reactor, said tubular reactor comprising:
 a first reaction zone having an inlet for said gas mixture and a second reaction zone having an outlet for reaction gas mixture containing maleic anhydride, wherein the first reaction zone precedes the second reaction zone in a direction of flow of the gas mixture,
 a plurality of tubes extending in an axial direction through said first and second reaction zones and communicatively connected with said inlet and said outlet with respective first and second ends thereof;
 a temperature control system configured for controlling a reaction temperature in each of the reaction zones independently, wherein the temperature control system comprises:
  a heat transfer system for each of the reaction zones configured for controlling the temperature of a liquid coolant flowing through one of the reaction zones; and;
  a circulation pumping system configured for controlling flow conditions of the liquid coolant flowing through the reactor and through one of the heat transfer systems; and
 a preheating arrangement configured for preheating the gas mixture such that the gas mixture enters the first reaction zone at a predefined inlet temperature;
wherein the axial length of the tubes within said first reaction zone corresponds to between 30% and 45% of the total length covered by the tubes within said first and second reaction zones; under the proviso that the inlet temperature and the proportions of the length of the tubes arranged in said first and second reaction zones are such that a total heat generated by the exothermic reactions inside the first reaction zone is equal or larger than an amount of heat required for preheating the gas mixture to the predefined inlet temperature, wherein the liquid coolant flows within at least one reaction zone at a flowing velocity that increases along the direction of flow of the gas mixture;
wherein the method comprises the steps of:
 setting the temperature of a liquid coolant flowing through the reactor in each of the reaction zones independently by means of the heat transfer systems;
 setting the flow conditions of the liquid coolant by means of the circulation pumping system;
 preheating the gas mixture such that the gas mixture enters the reactor at a predefined inlet temperature by means of the preheating arrangement; and
 setting the inlet temperature such that a total heat generated by the exothermic reaction inside the first reaction zone is equal or larger than an amount of heat required for preheating the gas mixture to the predefined inlet temperature.

35. The method of claim 34, wherein the reactor further comprises a plurality of baffles installed inside the reactor and configured for directing a meandering flow of the liquid coolant through the reactor, wherein an axial distance between pairs of adjacent baffles decreases along the direction of flow of the gas mixture within said at least one reaction zone.

* * * * *